(12) United States Patent
Bollard et al.

(10) Patent No.: US 9,885,021 B2
(45) Date of Patent: Feb. 6, 2018

(54) GENERATION OF BROADLY-SPECIFIC, VIRUS-IMMUNE CELLS TARGETING MULTIPLE HIV ANTIGENS FOR PREVENTIVE AND THERAPEUTIC USE

(71) Applicant: Children's National Medical Center, Washington, DC (US)

(72) Inventors: Catherine M. Bollard, Bethesda, MD (US); Conrad Russell Y. Cruz, Bethesda, MD (US); Sharon Lam, Atlanta, GA (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 0 days.

(21) Appl. No.: 14/737,084

(22) Filed: Jun. 11, 2015

(65) Prior Publication Data

US 2015/0359876 A1 Dec. 17, 2015

Related U.S. Application Data

(60) Provisional application No. 62/011,393, filed on Jun. 12, 2014.

(51) Int. Cl.
| | |
|---|---|
| *C12N 7/00* | (2006.01) |
| *A61K 45/06* | (2006.01) |
| *C12N 5/0783* | (2010.01) |
| *C12N 5/0784* | (2010.01) |

(52) U.S. Cl.
CPC ............... *C12N 7/00* (2013.01); *A61K 45/06* (2013.01); *C12N 5/0636* (2013.01); *C12N 5/0638* (2013.01); *C12N 5/0639* (2013.01); *C12N 2501/22* (2013.01); *C12N 2501/2301* (2013.01); *C12N 2501/2304* (2013.01); *C12N 2501/2306* (2013.01); *C12N 2501/2307* (2013.01); *C12N 2501/2312* (2013.01); *C12N 2501/2315* (2013.01); *C12N 2501/25* (2013.01); *C12N 2501/998* (2013.01); *C12N 2740/16034* (2013.01)

(58) Field of Classification Search
None
See application file for complete search history.

(56) References Cited

U.S. PATENT DOCUMENTS

| | | |
|---|---|---|
| 2009/0137017 A1 | 5/2009 | Bonyhadi et al. |
| 2010/0266635 A1 | 10/2010 | Hanke et al. |
| 2013/0130971 A1 | 5/2013 | Fernandez Ortega et al. |
| 2013/0251720 A1 | 9/2013 | Clark et al. |

FOREIGN PATENT DOCUMENTS

WO   WO 2010/051521 A1   5/2010

OTHER PUBLICATIONS

Pancino et al., J. Infect. Dis., 2010, 202(53):S345-S350.*
Porichis et al., Curr. Opin. HIV AIDS, May 2011, 6(3):174-180.*
Qin et al., PNAS, 2003, 100(1):183-188.*
Kitchen et al., PNAS, 2004, 101(23):8727-8732.*
International Search Report and Written Opinion dated Nov. 23, 2015 in PCT/US15/35361 (with Search History).
Sharon Lam, et al., "Ex Vivo Expanded Multi-Specific Cytotoxic T Lymphocytes Derived From HIV+ Patients and HIV Negative Donors Using GMP Compliant Methodologies Recognize Multiple HIV Antigens and Suppress HIV Replication" Blood, vol. 122, No. 21, Nov. 15, 2013, 3 Pages.
Mohammed A. Sadat, et al., "Glycosylation, Hypogammaglobulinemia, and Resistance to Viral Infections" The New England Journal of Medicine, vol. 370, No. 17, Apr. 24, 2014, pp. 1615-1625.

* cited by examiner

*Primary Examiner* — Stacy B Chen
(74) *Attorney, Agent, or Firm* — Oblon, McClelland, Maier & Neustadt, L.L.P.

(57) ABSTRACT

Compositions for T cell-based immunotherapy of HIV, HIV-associated malignancies, HIV-associated viral infections, or other HIV-related complications. Modified T cells that are resistant to invasion or infection with HIV, such as T-cells modified to decrease or eliminate expression of mannosyl-oligosaccharide glucosidase enzyme ("MOGS"). Methods for producing such compositions by expanding HIV-specific T cells from different sources to recognize multiple HIV antigens.

24 Claims, 1 Drawing Sheet

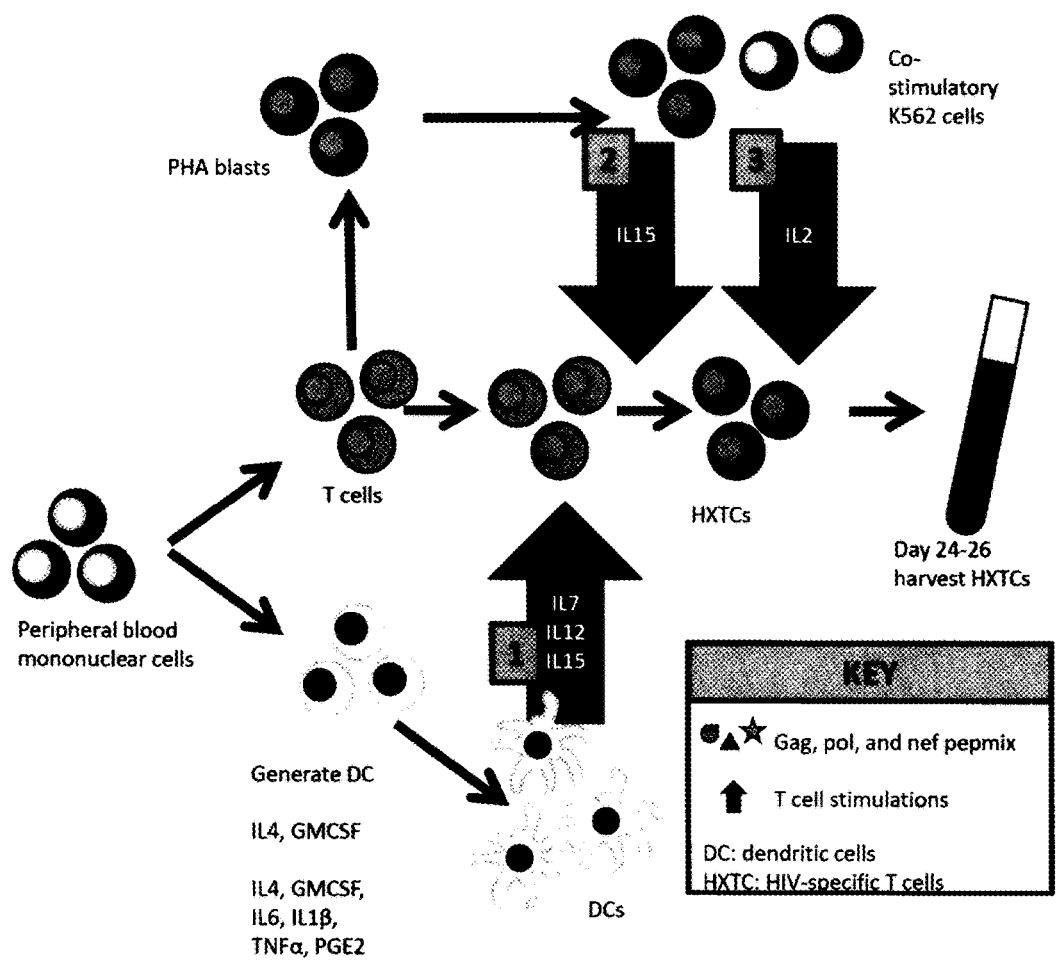

SEQUENCE LISTING

<160> NUMBER OF SEQ ID NOS: 2

<210> SEQ ID NO 1
<211> LENGTH: 2910
<212> TYPE: DNA
<213> ORGANISM: Homo sapiens
<220> FEATURE:
<221> NAME/KEY: CDS
<222> LOCATION: (164)..(2677)

<400> SEQUENCE: 1

```
acttccggcg ggaggcggag gcggaggcgc aggcgctggc tggcaggtgt cgctaaccgg      60 acgtggtcg ccagggcgag aggcgggagc cggagaggtg aggcaggacc cgggctccac     120
tgccgcctct ccgagctctt gtgacgcgga cctcagtgcc agg atg gct cgg ggc      175
                                              Met Ala Arg Gly
                                               1 gag cgg cgg cgc cgc gca gtg ccg gca gag gga gtg cgg aca gcc gag      223
Glu Arg Arg Arg Arg Ala Val Pro Ala Glu Gly Val Arg Thr Ala Glu
 5                  10                  15                  20 agg gcg gct cgg gga ggc ccc ggg cga cgg gac ggc cgg ggc ggc ggg      271
Arg Ala Ala Arg Gly Gly Pro Gly Arg Arg Asp Gly Arg Gly Gly Gly
                 25                  30                  35 ccg cgt agc acg gct gga gga gtg gct ctg gcc gtc gtg gtc ctg tct      319
Pro Arg Ser Thr Ala Gly Gly Val Ala Leu Ala Val Val Val Leu Ser
             40                  45                  50 ttg gcc ctg ggt atg tcg ggg cgc tgg gtg ctg gcg tgg tac cgt gcg      367
Leu Ala Leu Gly Met Ser Gly Arg Trp Val Leu Ala Trp Tyr Arg Ala
         55                  60                  65 cgg cgg gcg gtc acg ctg cac tcc gcg cct cct gtg ttg cct gcc gac      415
Arg Arg Ala Val Thr Leu His Ser Ala Pro Pro Val Leu Pro Ala Asp
 70                  75                  80 tcc tcc agc ccc gcc gtg gcc ccg gac ctc ttc tgg gga acc tac cgc      463
Ser Ser Ser Pro Ala Val Ala Pro Asp Leu Phe Trp Gly Thr Tyr Arg
 85                  90                  95                 100 cct cac gtc tac ttc ggc atg aag acc cgc agc ccg aag ccc ctc ctc      511
Pro His Val Tyr Phe Gly Met Lys Thr Arg Ser Pro Lys Pro Leu Leu
                105                 110                 115 acc gga ctg atg tgg gcg cag cag ggc acc acc ccg ggg act cct aag      559
Thr Gly Leu Met Trp Ala Gln Gln Gly Thr Thr Pro Gly Thr Pro Lys
            120                 125                 130 ctc agg cac acg tgt gag cag ggg gac ggt gtg ggt ccc tat ggc tgg      607
Leu Arg His Thr Cys Glu Gln Gly Asp Gly Val Gly Pro Tyr Gly Trp
        135                 140                 145 gag ttc cac gac ggc ctc tcc ttc ggg cgc caa cac atc cag gat ggg      655
Glu Phe His Asp Gly Leu Ser Phe Gly Arg Gln His Ile Gln Asp Gly
    150                 155                 160 gcc tta agg ctc acc act gag ttc gtc aag agg cct ggg ggt cag cac      703
Ala Leu Arg Leu Thr Thr Glu Phe Val Lys Arg Pro Gly Gly Gln His
165                 170                 175                 180 gga ggg gac tgg agc tgg aga gtg act gta gag cct cag gac tca ggt      751
Gly Gly Asp Trp Ser Trp Arg Val Thr Val Glu Pro Gln Asp Ser Gly
                185                 190                 195 act tct gcc ctc cct ttg gtc tcc ctg ttc ttc tat gtg gtg aca gat      799
Thr Ser Ala Leu Pro Leu Val Ser Leu Phe Phe Tyr Val Val Thr Asp
            200                 205                 210 ggc aag gaa gtc cta cta cca gag gtt ggg gcc aag ggg cag ttg aag      847
Gly Lys Glu Val Leu Leu Pro Glu Val Gly Ala Lys Gly Gln Leu Lys
        215                 220                 225 ttt atc agt ggg cac acc agt gaa ctt ggt gac ttc cgc ttt aca ctt      895
Phe Ile Ser Gly His Thr Ser Glu Leu Gly Asp Phe Arg Phe Thr Leu
```

```
              230                 235                 240
ttg cca cca acc agt cca ggg gat aca gcc ccc aag tat ggc agc tac    943
Leu Pro Pro Thr Ser Pro Gly Asp Thr Ala Pro Lys Tyr Gly Ser Tyr
245                 250                 255                 260 aat gtc ttc tgg acc tcc aac cca gga ctg ccc ctg ctg aca gag atg    991
Asn Val Phe Trp Thr Ser Asn Pro Gly Leu Pro Leu Leu Thr Glu Met
                265                 270                 275 gta aag agt cgc cta aat agc tgg ttt cag cat cgg ccc cca ggg gcc   1039
Val Lys Ser Arg Leu Asn Ser Trp Phe Gln His Arg Pro Pro Gly Ala
            280                 285                 290 ccc cct gaa cgc tac ctc ggc ttg cca gga tcc ctg aag tgg gag gac   1087
Pro Pro Glu Arg Tyr Leu Gly Leu Pro Gly Ser Leu Lys Trp Glu Asp
        295                 300                 305 aga ggt cca agt ggg caa ggg cag ggg cag ttc ttg ata cag cag gtg   1135
Arg Gly Pro Ser Gly Gln Gly Gln Gly Gln Phe Leu Ile Gln Gln Val
    310                 315                 320 acc ctg aaa att ccc att tcc ata gag ttt gtg ttt gaa tca ggc agt   1183
Thr Leu Lys Ile Pro Ile Ser Ile Glu Phe Val Phe Glu Ser Gly Ser
325                 330                 335                 340 gcc cag gca gga gga aat caa gcc ctg cca aga ctg gca ggc agt cta   1231
Ala Gln Ala Gly Gly Asn Gln Ala Leu Pro Arg Leu Ala Gly Ser Leu
                345                 350                 355 ctg acc cag gcc ctg gag agc cat gct gaa ggc ttt aga gag cgc ttt   1279
Leu Thr Gln Ala Leu Glu Ser His Ala Glu Gly Phe Arg Glu Arg Phe
            360                 365                 370 gag aag acc ttc cag ctg aag gag aag ggc ctg agc tct ggc gag cag   1327
Glu Lys Thr Phe Gln Leu Lys Glu Lys Gly Leu Ser Ser Gly Glu Gln
        375                 380                 385 gtt ttg ggt cag gct gcc ctc agc ggc ctc ctt ggt gga att ggc tac   1375
Val Leu Gly Gln Ala Ala Leu Ser Gly Leu Leu Gly Gly Ile Gly Tyr
    390                 395                 400 ttc tac gga caa ggg ctg gta ttg cca gac atc ggg gtg gaa ggg tct   1423
Phe Tyr Gly Gln Gly Leu Val Leu Pro Asp Ile Gly Val Glu Gly Ser
405                 410                 415                 420 gag cag aag gtg gac cca gcc ctc ttt cca ccc gta cct ctt ttt aca   1471
Glu Gln Lys Val Asp Pro Ala Leu Phe Pro Pro Val Pro Leu Phe Thr
                425                 430                 435 gca gtg ccc tcc cgg tca ttc ttc cca cga ggc ttc ctt tgg gat gaa   1519
Ala Val Pro Ser Arg Ser Phe Phe Pro Arg Gly Phe Leu Trp Asp Glu
            440                 445                 450 ggc ttt cac cag ctg gtg gtt cag cgg tgg gat ccc tcc ctc acc cgg   1567
Gly Phe His Gln Leu Val Val Gln Arg Trp Asp Pro Ser Leu Thr Arg
        455                 460                 465 gaa gcc ctt ggc cac tgg ctg ggg ctg cta aat gct gat ggc tgg att   1615
Glu Ala Leu Gly His Trp Leu Gly Leu Leu Asn Ala Asp Gly Trp Ile
    470                 475                 480 ggg agg gag cag ata ctg ggg gat gag gcc cga gcc cgg gtg cct cca   1663
Gly Arg Glu Gln Ile Leu Gly Asp Glu Ala Arg Ala Arg Val Pro Pro
485                 490                 495                 500 gaa ttc cta gta caa cga gca gtc cac gcc aac ccc cca acc cta ctt   1711
Glu Phe Leu Val Gln Arg Ala Val His Ala Asn Pro Pro Thr Leu Leu
                505                 510                 515 ttg cct gta gcc cat atg cta gag gtt ggt gac cct gac gac ttg gct   1759
Leu Pro Val Ala His Met Leu Glu Val Gly Asp Pro Asp Asp Leu Ala
            520                 525                 530 ttc ctc cga aag gcc ttg ccc cgc ctg cat gcc tgg ttt tcc tgg ctc   1807
Phe Leu Arg Lys Ala Leu Pro Arg Leu His Ala Trp Phe Ser Trp Leu
        535                 540                 545 cat cag agc cag gca ggc cca ctg cca cta tct tac cgc tgg cgg gga   1855
```

```
                His Gln Ser Gln Ala Gly Pro Leu Pro Leu Ser Tyr Arg Trp Arg Gly
                    550                 555                 560 cgg gac cct gcc tta cca acc tta ctg aac ccc aag acc cta ccc tct         1903
Arg Asp Pro Ala Leu Pro Thr Leu Leu Asn Pro Lys Thr Leu Pro Ser
565                 570                 575                 580 ggg ctg gat gac tac ccc cgg gct tca cac cct tca gta acc gag cgg         1951
Gly Leu Asp Asp Tyr Pro Arg Ala Ser His Pro Ser Val Thr Glu Arg
                585                 590                 595 cac ctg gac ctg cga tgt tgg gtg gca ctg ggt gcc cgt gtg ctg acg         1999
His Leu Asp Leu Arg Cys Trp Val Ala Leu Gly Ala Arg Val Leu Thr
            600                 605                 610 cgg ctg gca gag cat ctg ggt gag gct gag gta gct gct gag ctg ggc         2047
Arg Leu Ala Glu His Leu Gly Glu Ala Glu Val Ala Ala Glu Leu Gly
        615                 620                 625 cca ctg gct gcc tca ctg gag gca gca gag agc ctg gat gag ctg cac         2095
Pro Leu Ala Ala Ser Leu Glu Ala Ala Glu Ser Leu Asp Glu Leu His
    630                 635                 640 tgg gcc cca gag cta gga gtc ttt gca gac ttt ggg aac cac aca aaa         2143
Trp Ala Pro Glu Leu Gly Val Phe Ala Asp Phe Gly Asn His Thr Lys
645                 650                 655                 660 gca gta cag ctg aag ccc agg ccc cct cag ggg ctc gtt cgg gtg gtg         2191
Ala Val Gln Leu Lys Pro Arg Pro Pro Gln Gly Leu Val Arg Val Val
                665                 670                 675 ggt cgg ccc caa cct caa ctg cag tat gta gat gct ctt ggc tat gtc         2239
Gly Arg Pro Gln Pro Gln Leu Gln Tyr Val Asp Ala Leu Gly Tyr Val
            680                 685                 690 agt ctt ttt ccc ttg ctg ctg cga ctg ctg gac ccc acc tca tcc cgc         2287
Ser Leu Phe Pro Leu Leu Leu Arg Leu Leu Asp Pro Thr Ser Ser Arg
        695                 700                 705 ctt ggg ccc ctg ctg gac att cta gcc gac agc cgc cat ctc tgg agc         2335
Leu Gly Pro Leu Leu Asp Ile Leu Ala Asp Ser Arg His Leu Trp Ser
    710                 715                 720 ccc ttt ggt tta cgc tcc ctt gca gcc tcc agc tcc ttt tat ggc cag         2383
Pro Phe Gly Leu Arg Ser Leu Ala Ala Ser Ser Ser Phe Tyr Gly Gln
725                 730                 735                 740 cgc aat tca gag cat gat ccc ccc tac tgg cgg ggt gct gtg tgg ctc         2431
Arg Asn Ser Glu His Asp Pro Pro Tyr Trp Arg Gly Ala Val Trp Leu
                745                 750                 755 aat gtc aac tac ctg gct ttg gga gca ctc cac cac tat ggg cat ctg         2479
Asn Val Asn Tyr Leu Ala Leu Gly Ala Leu His His Tyr Gly His Leu
            760                 765                 770 gag ggt cct cac cag gct cgg gct gcc aaa ctc cac ggt gag ctc cgt         2527
Glu Gly Pro His Gln Ala Arg Ala Ala Lys Leu His Gly Glu Leu Arg
        775                 780                 785 gcc aac gtg gta ggc aat gta tgg cgc cag tac cag gct aca ggc ttt         2575
Ala Asn Val Val Gly Asn Val Trp Arg Gln Tyr Gln Ala Thr Gly Phe
    790                 795                 800 ctt tgg gag cag tac agt gac cgc gat ggg cga ggc atg ggc tgc cgc         2623
Leu Trp Glu Gln Tyr Ser Asp Arg Asp Gly Arg Gly Met Gly Cys Arg
805                 810                 815                 820 cct ttc cac ggc tgg acc agc ctt gtc tta ctg gcc atg gct gaa gac         2671
Pro Phe His Gly Trp Thr Ser Leu Val Leu Leu Ala Met Ala Glu Asp
                825                 830                 835 tac tga agggagggag aggaggggag ccaagacact catgccactc tggctctgaa         2727
Tyr gggacaaagg cttctggctt ttgccccag ccccttggat accagtaatt caaaccttcc       2787
tcatttcatc tcaggtgtct ccttgctgtc atcccacata gccctggggt gaatgtgaat      2847
ccagagtcta tttttctaaa taaattggaa aaaacatttt gaactctaaa aaaaaaaaa       2907
``` aaa    2910

<210> SEQ ID NO 2
<211> LENGTH: 837
<212> TYPE: PRT
<213> ORGANISM: Homo sapiens

<400> SEQUENCE: 2

Met Ala Arg Gly Glu Arg Arg Arg Ala Val Pro Ala Glu Gly Val
1               5                   10                  15

Arg Thr Ala Glu Arg Ala Ala Arg Gly Gly Pro Gly Arg Arg Asp Gly
            20                  25                  30

Arg Gly Gly Pro Arg Ser Thr Ala Gly Val Ala Leu Ala Val
            35                  40                  45

Val Val Leu Ser Leu Ala Leu Gly Met Ser Gly Arg Trp Val Leu Ala
50                  55                  60

Trp Tyr Arg Ala Arg Arg Ala Val Thr Leu His Ser Ala Pro Pro Val
65                  70                  75                  80

Leu Pro Ala Asp Ser Ser Ser Pro Ala Val Ala Pro Asp Leu Phe Trp
                85                  90                  95

Gly Thr Tyr Arg Pro His Val Tyr Phe Gly Met Lys Thr Arg Ser Pro
                100                 105                 110

Lys Pro Leu Leu Thr Gly Leu Met Trp Ala Gln Gln Gly Thr Thr Pro
            115                 120                 125

Gly Thr Pro Lys Leu Arg His Thr Cys Glu Gln Gly Asp Gly Val Gly
            130                 135                 140

Pro Tyr Gly Trp Glu Phe His Asp Gly Leu Ser Phe Gly Arg Gln His
145                 150                 155                 160

Ile Gln Asp Gly Ala Leu Arg Leu Thr Thr Glu Phe Val Lys Arg Pro
                165                 170                 175

Gly Gly Gln His Gly Gly Asp Trp Ser Trp Arg Val Thr Val Glu Pro
            180                 185                 190

Gln Asp Ser Gly Thr Ser Ala Leu Pro Leu Val Ser Leu Phe Phe Tyr
        195                 200                 205

Val Val Thr Asp Gly Lys Glu Val Leu Leu Pro Glu Val Gly Ala Lys
    210                 215                 220

Gly Gln Leu Lys Phe Ile Ser Gly His Thr Ser Glu Leu Gly Asp Phe
225                 230                 235                 240

Arg Phe Thr Leu Leu Pro Pro Thr Ser Pro Gly Asp Thr Ala Pro Lys
                245                 250                 255

Tyr Gly Ser Tyr Asn Val Phe Trp Thr Ser Asn Pro Gly Leu Pro Leu
            260                 265                 270

Leu Thr Glu Met Val Lys Ser Arg Leu Asn Ser Trp Phe Gln His Arg
        275                 280                 285

Pro Pro Gly Ala Pro Glu Arg Tyr Leu Gly Leu Pro Gly Ser Leu
    290                 295                 300

Lys Trp Glu Asp Arg Gly Pro Ser Gly Gln Gly Gln Gly Gln Phe Leu
305                 310                 315                 320

Ile Gln Gln Val Thr Leu Lys Ile Pro Ile Ser Ile Glu Phe Val Phe
                325                 330                 335

Glu Ser Gly Ser Ala Gln Ala Gly Asn Gln Ala Leu Pro Arg Leu
            340                 345                 350

Ala Gly Ser Leu Leu Thr Gln Ala Leu Glu Ser His Ala Glu Gly Phe
        355                 360                 365

```
Arg Glu Arg Phe Glu Lys Thr Phe Gln Leu Lys Glu Lys Gly Leu Ser
    370                 375                 380

Ser Gly Glu Gln Val Leu Gly Gln Ala Ala Leu Ser Gly Leu Leu Gly
385                 390                 395                 400

Gly Ile Gly Tyr Phe Tyr Gly Gln Gly Leu Val Leu Pro Asp Ile Gly
                405                 410                 415

Val Glu Gly Ser Glu Gln Lys Val Asp Pro Ala Leu Phe Pro Pro Val
                420                 425                 430

Pro Leu Phe Thr Ala Val Pro Ser Arg Ser Phe Phe Pro Arg Gly Phe
            435                 440                 445

Leu Trp Asp Glu Gly Phe His Gln Leu Val Val Gln Arg Trp Asp Pro
450                 455                 460

Ser Leu Thr Arg Glu Ala Leu Gly His Trp Leu Gly Leu Leu Asn Ala
465                 470                 475                 480

Asp Gly Trp Ile Gly Arg Glu Gln Ile Leu Gly Asp Glu Ala Arg Ala
                485                 490                 495

Arg Val Pro Pro Glu Phe Leu Val Gln Arg Ala Val His Ala Asn Pro
                500                 505                 510

Pro Thr Leu Leu Leu Pro Val Ala His Met Leu Glu Val Gly Asp Pro
            515                 520                 525

Asp Asp Leu Ala Phe Leu Arg Lys Ala Leu Pro Arg Leu His Ala Trp
530                 535                 540

Phe Ser Trp Leu His Gln Ser Gln Ala Gly Pro Leu Pro Leu Ser Tyr
545                 550                 555                 560

Arg Trp Arg Gly Arg Asp Pro Ala Leu Pro Thr Leu Leu Asn Pro Lys
                565                 570                 575

Thr Leu Pro Ser Gly Leu Asp Asp Tyr Pro Arg Ala Ser His Pro Ser
            580                 585                 590

Val Thr Glu Arg His Leu Asp Leu Arg Cys Trp Val Ala Leu Gly Ala
                595                 600                 605

Arg Val Leu Thr Arg Leu Ala Glu His Leu Gly Glu Ala Glu Val Ala
                610                 615                 620

Ala Glu Leu Gly Pro Leu Ala Ala Ser Leu Glu Ala Ala Glu Ser Leu
625                 630                 635                 640

Asp Glu Leu His Trp Ala Pro Glu Leu Gly Val Phe Ala Asp Phe Gly
                645                 650                 655

Asn His Thr Lys Ala Val Gln Leu Lys Pro Arg Pro Pro Gln Gly Leu
            660                 665                 670

Val Arg Val Val Gly Arg Pro Gln Pro Leu Gln Tyr Val Asp Ala
                675                 680                 685

Leu Gly Tyr Val Ser Leu Phe Pro Leu Leu Arg Leu Leu Asp Pro
            690                 695                 700

Thr Ser Ser Arg Leu Gly Pro Leu Leu Asp Ile Leu Ala Asp Ser Arg
705                 710                 715                 720

His Leu Trp Ser Pro Phe Gly Leu Arg Ser Leu Ala Ala Ser Ser Ser
                725                 730                 735

Phe Tyr Gly Gln Arg Asn Ser Glu His Asp Pro Pro Tyr Trp Arg Gly
                740                 745                 750

Ala Val Trp Leu Asn Val Asn Tyr Leu Ala Leu Gly Ala Leu His His
            755                 760                 765

Tyr Gly His Leu Glu Gly Pro His Gln Ala Arg Ala Ala Lys Leu His
    770                 775                 780
```

-continued

```
Gly Glu Leu Arg Ala Asn Val Val Gly Asn Val Trp Arg Gln Tyr Gln
785                 790                 795                 800

Ala Thr Gly Phe Leu Trp Glu Gln Tyr Ser Asp Arg Asp Gly Arg Gly
                805                 810                 815

Met Gly Cys Arg Pro Phe His Gly Trp Thr Ser Leu Val Leu Leu Ala
                820                 825                 830

Met Ala Glu Asp Tyr
            835
```

GENERATION OF BROADLY-SPECIFIC, VIRUS-IMMUNE CELLS TARGETING MULTIPLE HIV ANTIGENS FOR PREVENTIVE AND THERAPEUTIC USE

CROSS-REFERENCE TO RELATED APPLICATION

This application claims priority under 35 U.S.C. §119(e) to U.S. Provisional Application 62/011,393, filed Jun. 12, 2014, the contents of which are incorporated by reference in their entirety.

BACKGROUND OF THE INVENTION

Field of the Invention

The present invention is focused on the fields of immunotherapy and HIV/AIDS therapeutics. The invention directs a cell product that simultaneously targets multiple HIV antigens while remaining immune to the virus, the method used to generate this product, and its use in preventing and treating active and latent HIV infection, as well as HIV-associated malignancies. More specifically, the invention discloses a method for generation and ex vivo expansion of HIV-antigen specific T-cells that are treated or modified to decrease or eliminate expression of mannosyl-oligosacharide glucosidase enzyme (MOGS) thus rendering them resistant to infection by HIV.

Description of Related Art

Antiretroviral therapy (ART) prolongs the life of HIV-infected individuals by preventing the progression to severe immunodeficiency but ART cannot cure infection, and life-long therapy is necessary to provide continuous viral suppression. Populations that are at high risk for treatment non-adherence are vulnerable to drug resistance and further transmission of HIV, preventing the eradication of the virus on a global scale. Furthermore, the long-term use of ART can lead to side effects in the renal, hepatic, and cardiovascular systems [1]. Another reason why HIV continues to be a pandemic is the lack of an effective vaccine. The most successful vaccine trial to date only produced a marginally statistically significant efficacy of 31% for HIV prevention [2].

T-cells have been used to treat virus-associated cancers and viral reactivations post-transplant [3-7]. Although T-cells specific for HIV antigens have been produced, CD4$^+$ T-cells are susceptible to infection by HIV which enters the cell through a CD4-dependent mechanism.

The mannosyl-oligosacharide glucosidase (MOGS) enzyme is deficient in a disease called congenital disorder of glycosylation type IIb (CDG-IIb), where patients exhibit neurologic defects and hypogammaglobulinemia. Along with these gross manifestations however, is an intriguing resistance to viruses with glycan shields: most notably, HIV and influenza [8].

Drugs that interfere with host endoplasmic reticulum glucosidase activity have been used to reduce the infectivity of secreted virions [9]. Drugs that interfere with N-glycan processing have been proposed as ways to disrupt the morphogenesis of a broad spectrum of enveloped viruses [10]. Such drugs would also affect processing of N-glycans in host cells.

The effects of reducing or disabling expression of MOGS on the in vivo and ex vivo viability, robustness, and immunological properties of antigen-specific T-cells, and on the resistance of such T-cells to virus invasion and infection have not been previously reported. Thus, the capacity T-cell immunotherapies using such T-cells to treat cancer, viral diseases and other pathologies involving T-cells were not known.

BRIEF SUMMARY OF THE INVENTION

The present invention describes a cell product derived from any donor source that is HIV-resistant and simultaneously targets multiple HIV antigens and potentially multiple tumor and viral antigens, the method used to generate this product, and its use for preventing and treating HIV infection, HIV-associated malignancy, and HIV-associated infections. The product consists of non-adherent peripheral blood mononuclear cells that have been stimulated with antigen-presenting cells with peptides representing HIV antigens gag, pol, nef, and env and/or viral and tumor antigens associated with HIV-associated disease. These cells were grown in the presence of activating cytokines and feeder cells genetically modified to express co-stimulatory molecules that promote T cell proliferation and differentiation into effector memory cells. This product can be expanded to (1) mediate systemic resistance to HIV by knockdown of MOGS, and (2) improve anti-HIV, antiviral, and/or antitumor capabilities by combination with other therapies through combination with other cells.

Our strategy to prevent as well as treat HIV infection involves not only the administration of a vaccine but also the administration of cytotoxic T lymphocytes, (i.e., T cell immunotherapeutics), which have proven successful for the treatment of virus-associated cancers and viral reactivations post-transplant [3-7]. Cytotoxic T lymphocytes are immune cells that are responsible for killing virus-infected cells. They recognize non-self proteins (antigens) that are expressed on target cells during infection and kill by producing a variety of inflammatory proteins that form holes on the cell surface, trigger cell death, and stimulate other immune cells to become activated. Furthermore, they have the ability to become memory cells which produce a more rapid and robust response against viral infection. The activation of such memory cells is responsible for the efficacy of vaccines in preventing infections like influenza, for example.

T cell immunotherapy utilizes these immune cells because they have the ability to proliferate in vivo, and persist long-term as memory cells. This type of therapy consists of redirecting the specificity of T lymphocytes or enriching for pre-existing antigen-specific T lymphocytes ex vivo and expanding these antigen-specific T lymphocytes from patients until a sufficient number of cells are obtained for reinfusion. While the use of T lymphocytes has proven to be effective in the cancer and post-transplant setting, most T cell therapies for HIV so far have only shown safety without the ability to control viral load long-term [11-13]. In a recent study where T cell expression of the CCR5 HIV entry co-receptor has been abrogated, longer T cell persistence is seen. However, effects on viral load after ART treatment interruption do not show significant decreases from their peak levels with the possible exception of one patient where a 2.1 log decrease was seen. However, this patient has been found to be heterozygous for CCR5 delta32; it is unclear how this has impacted the findings [14].

Two possible reasons for the decreased efficacy seen with this approach so far are: (1) the use of single epitopes or antigens to target HIV, and (2) the sole use of CD8+ cytotoxic T cells. Using T-cells targeting single epitopes inherently limits the number of targetable HIV infected cells, and increases the risks for viral escape and subsequent resistance to the immunotherapy. Further, using only CD8+ T cells eliminates the T-cell help provided by CD4+ T cells. Single antigens have traditionally been used because of the difficulty of generating polyclonal populations in culture, thought to be the result of immunodominant antigens competing with less immunogenic antigens, while the sole use of CD8+ T cells allows circumvention of the viral tropism towards CD4+ T cells since infused CD4 T cells will theoretically be additional targets for viral infection.

Using Multiple Antigens.

Cells administered in HIV clinical trials thus far have largely been single epitope specific CD3+CD8+ pre-selected T lymphocyte clones expanded in the presence of mitogens [11, 12]. This is in contrast to the administration of polyclonal virus specific T lymphocytes derived from unselected, peripheral blood mononuclear cells expanded in the presence of whole antigen and growth cytokines that have been successful at targeting EBV [3, 4], CMV, and adenovirus [5-7] in the cancer and post-transplant settings. Hence, we propose that developing an HIV-specific immune cell product containing T lymphocytes with broader recognition would not only increase the ability of the T lymphocytes to target infected cells but also provide antigenic stimulation to enhance the in vivo persistence of these cells. Furthermore, because the majority of these cells generated with our method have a memory phenotype, they can also be infused prior to HIV infection to provide a vaccine-like protection against infection.

Conferring Immunity to HIV.

Susceptibility of CD4 T cells to HIV has been addressed by conferring resistance using genetic modification of the T cells. One key mechanism we employed to increase systemic resistance against HIV involves the disruption of the mannosyl-oligosacharide glucosidase enzyme (MOGS) expression.

A representative MOGS amino acid sequence is encoded by SEQ ID NO: 1 and described by NM_006302.2; GI:149999605 and SEQ ID NO: 2 describes the corresponding MOGS amino acid sequence. Information about these MOGS sequences is incorporated by reference to these accession numbers and database entries (last accessed Jun. 9, 2015). A MOGS amino acid sequence is also described by NCBI Reference Sequence: NP_006293.2; GI: 149999606 (mannosyl-oligosaccharide glucosidase isoform 1 [*Homo sapiens]*; 837 aa protein; Chromosome: 2.Map: 2p13.1). Information about this MOGS sequence is incorporated by reference to these accession numbers and database entries (last accessed Jun. 9, 2015).

MOGS is a carbohydrate enzyme involved in the processing of N-linked oligosaccharides which is a key process during the coating of the viral particle with its glycan shield. If this process is disrupted, the resulting viral particles have defective glycan shields, and therefore cannot enter CD4 T cells. Moreover, these viral particles are effectively less virulent. The enzyme is deficient in a disease called congenital disorder of glycosylation type IIb (CDG-IIb), where patients exhibit neurologic defects and hypogammaglobulinemia. Along with these gross manifestations however, is an intriguing resistance to viruses with glycan shields: most notably, HIV and influenza [8].

HIV-specific T cells deficient in MOGS were designed. MOGS may be knocked down in T cells using a combination of any of the following technologies: RNAi, CRISPR, TALENS, zinc finger nucleases, expression of intrabodies, and co-administration of drugs that targets MOGS (castanospermine, N-butyldeoxynojirimycin, or deoxynojirimycin). Knockout or knockdown strategies used for example to remove CCR5 as described by Cannon et al [15] are also incorporated thereto.

The genetic modification of T cells has been successfully used in the cancer setting, more specifically in the chimeric antigen receptor platform, using a variety of methods (transposon-mediated, retroviral-mediated, lentiviral-mediated)—see Duong C P, et al. [16]which is incorporated by reference.

In other disease settings, genetic modification does not alter the function of antigen-specific T cells [17]. Thus, we foresee that genetic modification of HIV-specific T cells should confer additional HIV-resistance properties without altering their anti-HIV function.

Although similar approaches using knockdown of the entry receptors CCR5 and CXCR4 also resulted in HIV-immune T cells, knockdown of these proteins limits cellular resistance to virus strains with tropism towards the relevant receptor.

Disruption of MOGS expression, on the other hand, would provide a more global systemic resistance towards potentially all strains of HIV. To date, while no demonstrable product demonstrated the potential superiority of this approach, the findings in patients with genetic deficiencies in MOGS were especially encouraging. In these patient cells, MOGS knockdown resulted in fewer viruses released when compared to healthy controls (3.6 to 89 times higher in controls), and infectivity of virus was decreased 50 to 80% [8]. MOGS knockdown will thus theoretically not only confer systemic resistance to the virus, but has the advantage of making newly synthesized virions less virulent.

Our invention consists of functional, broadly-specific virus-resistant T lymphocytes cell products from both HIV positive and negative individuals generated in a single culture to target gag, pol, nef, and envelope antigens of HIV and/or tumor antigens expressed on HIV-associated tumors, the method we developed to generate this product, and their clinical use.

BRIEF DESCRIPTION OF THE DRAWINGS

FIG. 1. Schematic of method for generating HIV-specific T cells. The method of expanding HIV-specific T cells is presented, using overlapping peptides spanning the HIV proteins Gag, Pol, Nef, and Env presented by dendritic cells and autologous PHA blasts or CD3/28 blasts. T cells are grown in the presence of indicated cytokines and feeder cells at each stimulation. Peptides are also presented by dendritic cells and autologous PHA blasts or CD3/28 blasts. T cells are grown in the presence of indicated cytokines and feeder cells at each stimulation. MOGS expression or activity in the HIV-antigen specific T-cells recovered by this method has been or is knocked down, attenuated, or knocked out by genetic modification of the T-cells, T-cell precursors, or HIV-antigen specific T-cells or by contacting these cells with one or more drugs or agents that inhibit or block MOGS expression or activity.

DETAILED DESCRIPTION OF THE INVENTION

"Accessory cell" or "Feeder cell" is a cell, such as a K562 cell, that provides costimulation for recognition of peptide antigens by T-cells or that otherwise assists a T-cell recognize, become primed or expand in the presence of a peptide antigen.

An "antigen" includes molecules, such as polypeptides, peptides, or glyco- or lipo-peptides that are recognized by the immune system, such as by the cellular or humoral arms of the human immune system. The term "antigen" includes antigenic determinants, such as peptides with lengths of 6, 7, 8, 9, 10, 11, 12, 13, 14, 15, 16, 17, 18, 19, 20, 21, 22 or more amino acid residues that bind to MHC molecules, form parts of MHC Class I or II complexes, or that are recognized when complexed with such molecules. Examples of antigens include peptides or peptide fragments encoded by HIV gag, pol, nef, and env genes and viral and tumor antigens associated with HIV-associated disease.

An "antigen presenting cell (APC)" refers to a class of cells capable of presenting one or more antigens in the form of peptide-MHC complex recognizable by specific effector cells of the immune system, and thereby inducing an effective cellular immune response against the antigen or antigens being presented. Examples of professional APCs are dendritic cells and macrophages, though any cell expressing MHC Class I or II molecules can potentially present a peptide antigen.

A "control" is a reference sample or subject used for purposes of comparison with a test sample or test subject. Positive controls measure an expected response and negative controls provide reference points for samples where no response is expected.

The term "cytokine" has its normal meaning in the art. Examples of cytokines used in the invention include IL-2, IL-7 and IL-15.

The term "dendritic cell" or "DC describes a diverse population of morphologically similar cell types found in a variety of lymphoid and non-lymphoid tissues[18]. One embodiment of the invention involves dendritic cells and dendritic cell precursors derived from the blood of an HIV-negative or HIV-positive donor.

The term "effector cell" describes a cell that can bind to or otherwise recognize an antigen and mediate an immune response. Antigen-specific T-cells are effector cells.

The term "isolated" means separated from components in which a material is ordinarily associated with, for example, an isolated cord blood mononuclear cell can be separated from red blood cells, plasma, and other components of blood.

The term "MOGS" refers to the enzyme mannosyl-oligosacharide glucosidase, preferably, human variants of this enzyme. A representative sequence for MOGS is given by SEQ ID NO: 1. MOGS analogs or homologs, such as allelic variants or mammalian homologs to human MOGS, may have 70%, 75%, 80%, 85%, 87.5%, 90%, 91%, 92%, 93%, 94%, 95%, 96%, 97%, 98%, 99% and up to 100% sequence identity or sequence similarity with SEQ ID NO: 1. BLASTP may be used to identify an amino acid sequence having at least 70%, 75%, 80%, 85%, 87.5%, 90%, 92.5%, 95%, 97.5%, 98%, 99% sequence similarity to a reference amino acid sequence, such as that of SEQ ID NO: 1, using a similarity matrix such as BLOSUM45, BLOSUM62 or BLOSUM80. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure.

Nucleic acids encoding MOGS are described by reference to the MOGS amino acid sequences described herein and the genetic code. Such nucleic acids may be produced by chemical synthesis, by molecular biological, or by recombinant methods well known in the art. Such polynucleotides may be incorporated into vectors or DNA constructs and used to knock out or modify the expression of MOGS in a cell. Such MOGS sequences may have 70%, 75%, 80%, 85%, 87.5%, 90%, 91%, 92%, 93%, 94%, 95%, 96%, 97%, 98%, 99% and up to 100% sequence identity with the MOGS sequence of SEQ ID NO: 2. Polynucleotide fragments of such sequences useful for modifying or knocking out cellular MOGS expression also contemplated. Such sequences may be designed to attenuate or knock out MOGS expression or to replace all or part of a MOGS sequence in a cell. The degree of identity between two nucleic acid sequences can be determined using the BLASTn program for nucleic acid sequences, which is available through the National Center for Biotechnology Information (http://_www.ncbi.nlm.nih.gov/blast/Blast.cgi?PAGE=Nucleotides) (last accessed Jun. 9, 2015). The percent identity of two nucleotide sequences may be made using the BLASTn preset "search for short and near exact matches" using a word size of 7 with the filter off, an expect value of 1,000 and match/mismatch of 2/-3, gap costs existence 5, extension 2; or standard nucleotide BLAST using a word size of 11, filter setting "on" (dust) and expect value of 10.

A "naive" T-cell or other immune effector cell is one that has not been exposed to an antigen or to an antigen-presenting cell presenting a peptide antigen capable of activating that cell.

A "peptide library" or "overlapping peptide library" within the meaning of the application is a complex mixture of peptides which in the aggregate covers the partial or complete sequence of a protein antigen, especially those of opportunistic viruses. Successive peptides within the mixture overlap each other, for example, a peptide library may be constituted of peptides 15 amino acids in length which overlapping adjacent peptides in the library by 11 amino acid residues and which span the entire length of a protein antigen. Peptide libraries are commercially available and may be custom-made for particular antigens. Methods for contacting, pulsing or loading antigen-presenting cells are well known and incorporated by reference to Ngo, et al.[19].

The term "precursor cell" refers to a cell which can differentiate or otherwise be transformed into a particular kind of cell. For example, a "T-cell precursor cell" can differentiate or mature into a T-cell and a "dendritic precursor cell" can differentiate or mature into a dendritic cell.

A "subject" is a vertebrate, preferably a mammal, more preferably a human. Mammals include, but are not limited to humans, simians, equines, bovines, porcines, canines, felines, murines, farm animals, livestock, sport animals, or pets. Subjects include those in need of antigen-specific T-cells resistant to invasion by HIV, such as those infected by HIV or having AIDS or AIDS-associated opportunistic infections or malignancies.

EMBODIMENTS

Nonlimiting embodiments of the invention include the following.

1. A method for producing HIV-antigen-specific T cell(s) resistant to infection by HIV comprising:

(a) separating T-cells or T-cell precursors (e.g., CD3+ cells or cells that do not adhere to plastic) and dendritic cells or dendritic cell precursors (e.g., CD11C+ cells, CD14+ cells, or cells that do adhere to plastic) in a hematopoietic cell sample, (b) producing blasts by contacting a portion of a hematopoietic cell sample or a portion of said separated T-cells or T-cell precursors with PHA or another mitogen, or by CD3/CD28 stimulation, and, optionally, treating the blasts with radiation or another agent to inhibit their outgrowth;

(c) contacting the dendritic cells or dendritic precursor cells separated in (a) with cytokine(s) or other agent(s) that generate and mature dendritic cells and with at least one HIV peptide antigen to produce HIV-antigen-presenting dendritic cells that present at least one HIV-peptide antigen, and, optionally, treating said HIV-antigen-presenting dendritic cells with radiation or another agent sufficient to inhibit their outgrowth;

(d) contacting the T-cells or T-cell precursors from (a) with the dendritic antigen-presenting cells produced in (c) in the presence of IL-2, IL-6, IL-7, IL-12, IL-15, and/or IL-21, preferably in the presence of IL-7, IL-12 and/or IL-15 to produce HIV-antigen-specific T-cells that recognize the at least one HIV-peptide antigen;

(e) contacting HIV-antigen-specific T-cells produced by (d) with the blasts of (b) in the presence of the at least one HIV-peptide antigen, optionally, in the presence of K562 cells, which may express costimulatory molecules, or other accessory or feeder cells and in the presence of IL-2, IL-6, IL-7, IL-12, IL-15, and/or IL-21, and preferably in the presence of IL-2 and/or IL-15;

(f) optionally, repeating (e) one or more times to restimulate and/or expand the HIV-antigen specific T-cells; and (g) recovering HIV-antigen-specific T-cells that recognize the at least one HIV-peptide antigen;

wherein the expression of mannosyl-oligosacharide glucosidase ("MOGS") in said T-cells, T-cell precursors, or HIV-antigen specific T-cells has been knocked down compared to MOGS expression in otherwise identical cells which has not been knocked down.

2. The method of embodiment 1, wherein the hematopoietic cell sample is a cord blood sample or other sample containing naïve immune cells.

3. The method of embodiment 1, wherein the hematopoietic cell sample is obtained from a peripheral blood sample from a donor who is HIV-negative.

4. The method of embodiment 1, wherein the hematopoietic cell sample is obtained from a peripheral blood sample from a donor who is HIV-positive, who has AIDS, or who has an HIV-associated infection or malignancy.

5. The method of embodiment 1, wherein in (b) the blasts are produced using PHA, conconavalin A, pokeweed mitogen, or another mitogen.

6. The method of embodiment 1, wherein in (b) the blasts are CD3/CD28 blasts produced by stimulating CD3/CD28.

7. The method of embodiment 1, wherein in (b) the blasts are irradiated or chemically treated to prevent their outgrowth.

8. The method of embodiment 1, wherein in (c) the separated dendritic cells or dendritic cell precursors are cultured in a dendritic cell medium containing IL-4 and GM-CSF, and then subsequently matured in a dendritic cell medium containing a mixture of IL-4, GM-CSF, IL-1B, IL-4, IL-6, PGE2, and/or TNF-α.

9. The method of embodiment 1, wherein in (c) the dendritic cells are contacted with HIV Gag, Pol, Nef and/or Env peptides or HIV Gag, Pol, Nef and/or Env peptide libraries. For example, the dendritic cells or their precursors may be contacted with overlapping peptides spanning the HIV proteins encoded by gag, pol, and nef as sources of antigen presented by dendritic cells in the first stimulation.

10. The method of embodiment 1, wherein in (c) the dendritic cells are further contacted with HIV Gag, Pol, Nef and Env peptides or HIV Gag, Pol, Nef and Env peptide libraries.

11. The method of embodiment 1, wherein in (d) the T-cells or T-cell precursors from (a) are contacted with the dendritic antigen-presenting cells produced in (c) in the presence of IL-7, IL-12 and IL-15 to produce HIV-antigen-specific T-cells that recognize the at least one HIV-peptide antigen.

12. The method of embodiment 1, wherein in (e) the HIV-antigen-specific T-cells from (d) are maintained in a medium containing IL-2.

13. The method of embodiment 1, wherein in (e) the HIV-antigen-specific T-cells from (d) are maintained in a medium containing IL-15.

14. The method of embodiment 1, wherein in (e) the HIV-antigen-specific T-cells from (d) are contacted with blasts that have been pulsed with HIV Gag, Pol, Nef and/or Env peptides or HIV Gag, Pol, Nef and/or Env peptide libraries.

15. The method of embodiment 1, wherein in (e) the HIV-antigen-specific T-cells from (d) are contacted and restimulated with blasts that have been pulsed with HIV Gag, Pol, Nef and/or Env peptides or HIV Gag, Pol, Nef and/or Env peptide libraries at least three times every 5-8 days.

16. The method of embodiment 1, wherein the hematopoietic cell sample has been obtained from an HIV-positive subject and steps (d) and/or (e) are performed in a medium containing amprenavir or another drug or agent that inhibits HIV replication.

17. The method of embodiment 1, wherein MOGS expression has been knocked down by contacting, maintaining or culturing the T-cells, precursor T-cells or HIV-antigen specific T-cells in a medium containing a drug that inhibits or inactivates MOGS. Examples of such drugs include castanospermine, N-butyldeoxynojirimycin, and deoxynojirimycin.

18. The method of embodiment 1, wherein MOGS expression has been knocked down by genetically modifying the T-cell, T-cell precursor, or HIV-antigen specific T-cell to attenuate or knock out MOGS expression; or by modifying the T-cell, T-cell precursor, or HIV-antigen specific T-cell using RNAi or by expression of intrabodies to attenuate or knock out MOGS expression.

19. A composition comprising HIV-antigen specific T-cells which recognize two, three, four or more different HIV antigens. This composition may be a cell product, derived from a healthy HIV-seronegative donor, or from an HIV-positive subject or patient with AIDS, expanded ex vivo to allow specific recognition of the HIV antigens encoded by the gag, pol, nef, and env genes, or by any combination of the four. This composition may conveniently be made according to the methods described herein, such as the method of embodiment 1.

The composition may comprise T-cells or T-cell precursors that recognize antigens other than, or in addition to, HIV antigens, such as antigens from viruses or pathogens associated with HIV infection, such opportunistic pathogens, tumor antigens including HIV-associated tumors, neoplasms or malignancies, or other antigens that can be recognized by T-cells.

Examples of tumor antigens include cancer testis antigens (survivin, MAGEA4, SSX2, PRAME, NYESO1), pluripotency factors (Oct4, Sox2, Nanog) and tumor protein p53 and MYCN tumor-associated antigen.

Examples of viral antigens include cytomegalovirus ("CMV") antigens pp65, IE1, UL40, UL103, UL151, UL153, UL28, UL32, UL36, UL55, UL40, UL48, UL82, UL94, UL99, us24, us32; herpes simplex antigens ("HSV") glycoprotein G; Epstein Barr Virus antigens BARF1, BMLF1, BMRF1, BZLF1, EBNALP, EBNA1, EBNA2, EBNA3A, EBNA3B, EBNA3C, gp350/340, LMP1, and LMP2; Human Herpes Virus 8 ("HHV8", which is associated with Kaposi's sarcoma) antigens LNA-1, LANA-1, viral cyclin D, vFLIP, RTA; Human Papilloma Virus 16 ("HPV16") antigens E6, E7, and L1 and Human Papilloma Virus 18 ("HPV16") antigens E6 and E7.

The cells in the composition may be rendered resistant to HIV infection by knockdown of MOGS. MOGS knockdown may be brought about by recognition of relevant mRNA, such as mRNA encoding MOGS or enzymes necessary for MOG activity, by a complementary RNA molecule, and mediated by RNA interference. For example, molecules encoding interfering RNA (RNAi) may be introduced into a T-cell or T-cell precursor by a suitable vector, such as a lentiviral or retroviral vector.

Knockdown or disruption of functional expression of MOGS may be brought about by guide DNA recognizing the MOGS gene, packaged with a clustered regularly interspaced short palindromic repeat cas9 or a modified cas9 gene.

It may be accomplished by introducing into a T-cell or T-cell precursor TALENS, CRISPR or zinc-finger nuclease products that disrupt a gene encoding MOGS or a gene necessary for its activity, for example, by transformation or transfection with a lentivirus or retrovirus vector encoding these products.

Knockdown or disruption of functional expression of MOGS may be brought about by guide DNA recognizing the MOGS gene, packaged with a clustered regularly interspaced short palindromic repeat cas9 or a modified cas9 gene fused with a transcriptional repressor such as KRAB.

Knockdown or disruption of functional expression of MOGS may be brought about by guide DNA recognizing the MOGS gene, packaged with a clustered regularly interspaced short palindromic repeat dcas9 or a modified dcas9 gene.

Knockdown or disruption of functional expression of MOGS may also brought about by recognition genomic DNA by engineered transcription activator-like effectors recognizing the MOGS gene.

Knockdown or disruption of functional expression of MOGS can be brought about by introduction of transgenes coding for MOGS-specific intrabodies, for example, by introduction into a T-cell or T-cell precursor a lentivirus or retrovirus vector encoding an intrabody that disrupts MOGS expression or activity.

Alternatively, a T-cell, T-cell precursor, or antigen-specific T-cell may be co-cultured with a drug that inhibits, blocks or attenuates MOGS expression or activity, such as the drugs castanospermine, N-butyldeoxynojirimycin, or deoxynojirimycin.

20. A method for inhibiting HIV invasion and replication in a subject or for treating a subject infected by HIV comprising administering the composition according to embodiment 19, optionally in combination with a drug or agent that attenuates or knocks out MOGS expression, to a subject in need thereof. This method may be used to prevent or treat HIV infections or HIV-associated conditions. A subject may be selected from those who are HIV-negative, but at risk for acquiring an HIV infection, an HIV-positive subject, a patient with AIDS or an HIV-associated malignancy, HIV-associated infection, and a complication of HIV.

HIV-antigen specific T-cells, such as those produced by the method according to embodiment 1 may be infused into a subject, for example, by intravenous infusion. A single or multiple infusions may be made. Prior to infusion, a subject or patient may be lymphodepleted, for example, by the administration of a drug such as cyclophosphamide, fludarabine, alemtusumab, by other lymphodepleting drugs, or by radiation. Immunomodulatory drugs, such as proteasome inhibitors, monoclonal antibodies, cytokines, anti-inflammatory drugs, or epigenetic-modifying drugs, may be administered to a subject or patient before, during or after an infusion of antigen-specific T-cells. Examples of epigenetic modifying drugs include the classes of histone deacetylase inhibitors and histone demethylase inhibitors.

Other cellular products may be coadministered with the antigen-specific T-cells according to the invention, such as adipose-derived, bone marrow derived, or dental pulp derived mesenchymal stem cells. Drugs that knockdown MOGS expression, such as castanospermine, N-butyldeoxynojirimycin or deoxynojirimycin may be administered before, during or after administration of antigen-specific T-cells according to the invention.

EXAMPLE

Generation of Virus-Resistant HIV-Specific Cytotoxic T Cells

Donors

Blood is collected from HIV-negative and HIV-positive human subjects. Umbilical cord blood is also obtained which is often used as a stem cell source for patients eligible for hematopoietic stem cell transplant. Blood is generally collected in 60 to 100 ml heparinized tubes or EDTA-containing tubes.

Isolation of Mononuclear Cells

Peripheral blood mononuclear cells ("PBMCs") are isolated from the blood of HIV-negative and HIV-positive subjects by density gradient centrifugation. The buffy coat containing PBMCs is removed from sedimented red blood cells and other plasma components and used to produce HIV-antigen specific T-cells. The isolated PBMCs may be preserved for later use by suspension in a cryopreservation medium such as a medium containing fetal bovine serum and dimethylsulfoxide (DMSO) by procedures known in the art.

Generation of Antigen Presenting Cells

PBMC were plated on 6 well plates and incubated for 2 hours in dendritic cell media (CellGenix DC media; CellGenix) supplemented with 2 mmol/L GlutaMax (Invitrogen). Nonadherent cells were harvested and cryopreserved. Adherent cells were cultured in dendritic cell media in the presence of interleukin (IL)-4 (1,000 U/mL) and granulocyte macrophage colony-stimulating factor (GM-CSF; 800 U/mL; both R&D). On day 5, immature dendritic cells were matured in dendritic cell media with a cytokine cocktail consisting of IL-4 (1,000 U/mL), GM-CSF (800 U/mL), IL-6 (100 ng/mL), TNF-α (10 ng/mL), IL-1β (10 ng/mL; all R&D), and PGE2 (1 μg/mL; Sigma-Aldrich), and were harvested after 24-48 hours of maturation for use as APC. To generate PHA-blasts, PBMC were stimulated with the mitogen PHA-P (5 μg/mL; Sigma-Aldrich) in presence of IL-2 to promote blast formation (PHA-blasts). PHA-blasts were cultured in RPMI-1640 supplemented with 10% human serum (Valley Medical), 2 mmol/L GlutaMax, and IL-2 (100 U/mL; R&D). To prevent possible viral outgrowth when cells were grown from HIV+individuals, PHA blasts were cultured in presence of 0.5 ng/mL of amprenavir.

Generation of HIV-Specific Cytotoxic T Cells (HXTC)

Matured dendritic cells were harvested and used as APC and simultaneously peptide-pulsed with gag, pol, nef and/or env peptide libraries (PepMix; JPT Peptide Technologies). Dendritic cells were used at a stimulator-to-effector ratio of 1:10. T cells were cultured in RPMI-1640 supplemented with 40% Clicks media (Irvine Scientific), 10% human AB serum, and 2 mmol/L GlutaMax. For initial stimulation, a cytokine mix containing IL-7 (10 ng/mL), IL-12 (10 ng/mL), IL-15 (5 ng/mL) (all R&D) was added. T cells were restimulated with peptide-pulsed autologous irradiated (30 Gy) PHA-blasts at a ratio of 1:4 on day 10 to 12 and cultures were maintained in IL-15 (5 ng/mL)-supplemented media or IL-2 (50 U/mL)-supplemented media and restimulated every 7 days as described previously for 3 stimulation cycles. HXTCs derived from HIV+patients were also expanded in presence of 0.5 ng/mL of amprenavir.

Generation of HIV-Specific and Tumor/Virus-Specific Cytotoxic T Cells (HXTC-T and HXTC-V)

Similar to the method above, matured dendritic cells were harvested and used as APC and simultaneously peptide-pulsed with gag, pol, nef and/or env and any combination of the following tumor antigens (survivin, MAGEA4, SSX2, PRAME, Oct4, Sox2, Nanog, p53, MYCN, and NYESO1 peptide libraries) or viral antigens (pp65, IE1, IE1, UL40, UL103, UL151, UL153, UL28, UL32, UL36, UL55, UL40, UL48, UL82, UL94, UL99, us24, us32, us32, HSV-1 glycoprotein G, BARF1, BMLF1, BMRF1, BZLF1, EBNALP, EBNA1, EBNA2, EBNA3A, EBNA3B, EBNA3C, gp350/340, LMP1, LMP2, LNA-1, LANA-1, viral cyclin D, vFLIP, RTA, E6, E7, and L1 peptide libraries) (PepMix; JPT Peptide Technologies). Dendritic cells are used at a stimulator-to-effector ratio of 1:10. T cells were cultured in RPMI-1640 supplemented with 40% Clicks media (Irvine Scientific), 10% human AB serum, and 2 mmol/L GlutaMax. For initial stimulation, a cytokine mix containing IL-7 (10 ng/mL), IL-12 (10 ng/mL), IL-15 (5 ng/mL) (all R&D) was added. T cells are restimulated with peptide-pulsed autologous irradiated (30 Gy) PHA-blasts at a ratio of 1:4 on day 10 to 12 and cultures are maintained in IL-15 (5 ng/mL)-supplemented media or IL-2(50 U/mL)-supplemented media and restimulated every 7 days as described previously for 3 stimulation cycles. HXTCs derived from HIV+ patients are also expanded in presence of 0.5 ng/mL of amprenavir.

Generation of Virus-Resistant HIV-Specific Cytotoxic T Cells (HXTC-R, HXTC-TR, and HXTC-VR)

T cells expanded according to the methods (HXTC, HXTC-T, and HXTC-V) above are subjected to disruption of MOGS expression, using any or a combination of the following procedures: RNAi, CRISPR, TALENS, expression of intrabodies, and co-administration of drugs that targets MOGS (castanospermine, N-butyldeoxynojirimycin, or deoxynojirimycin).

REFERENCES

1. Can, A., *Toxicity of antiretroviral therapy and implications for drug development*. Nat Rev Drug Discov, 2003. 2(8): p. 624-34.
2. Chung, A. W., et al., *Polyfunctional Fc-effector profiles mediated by IgG subclass selection distinguish RV144 and VAX003 vaccines*. Sci Transl Med, 2014. 6(228): p. 228ra38.
3. Bollard, C. M., et al., *In vivo expansion of LMP 1- and 2-specific T-cells in a patient who received donor-derived EBV-specific T-cells after allogeneic stem cell transplantation*. Leuk Lymphoma, 2006. 47(5): p. 837-42.
4. Bollard, C. M., et al., *Sustained complete responses in patients with lymphoma receiving autologous cytotoxic T lymphocytes targeting Epstein-Barr virus latent membrane proteins*. J Clin Oncol, 2014. 32(8): p. 798-808.
5. Leen, A. M., et al., *Multicenter study of banked third-party virus-specific T cells to treat severe viral infections after hematopoietic stem cell transplantation*. Blood, 2013. 121(26): p. 5113-23.
6. Leen, A. M., et al., *Cytotoxic T lymphocyte therapy with donor T cells prevents and treats adenovirus and Epstein-Barr virus infections after haploidentical and matched unrelated stem cell transplantation*. Blood, 2009. 114 (19): p. 4283-92.
7. Leen, A. M., et al., *Monoculture-derived T lymphocytes specific for multiple viruses expand and produce clinically relevant effects in immunocompromised individuals*. Nat Med, 2006. 12(10): p. 1160-6.
8. Sadat, M. A., et al., *Glycosylation, hypogammaglobulinemia, and resistance to viral infections*. N Engl J Med, 2014. 370(17): p. 1615-25.
9. Jordan, R., et al., *Inhibition of host ER glucosidase activity prevents Golgi processing of virion-associated bovine viral diarrhea virus E2 glycoproteins and reduces infectivity of secreted virions*. Virology, 2002. 295(1): p. 10-9.
10. Chang, J., T. M. Block, and J. T. Guo, *Antiviral therapies targeting host ER alpha-glucosidases: current status and future directions*. Antiviral Res, 2013. 99(3): p. 251-60.
11. Lieberman, J., et al., *Safety of autologous, ex vivo-expanded human immunodeficiency virus (HIV)-specific cytotoxic T-lymphocyte infusion in HIV-infected patients*. Blood, 1997. 90(6): p. 2196-206.
12. Chapuis, A. G., et al., *HIV-specific CD8+ T cells from HIV+ individuals receiving HAART can be expanded ex vivo to augment systemic and mucosal immunity in vivo*. Blood, 2011. 117(20): p. 5391-402.
13. Brodie, S. J., et al., *In vivo migration and function of transferred HIV-1-specific cytotoxic T cells*. Nat Med, 1999. 5(1): p. 34-41.
14. Tebas, P., et al., *Gene editing of CCR5 in autologous CD4 T cells of persons infected with HIV*. N Engl J Med, 2014. 370(10): p. 901-10.
15. Cannon, P. and C. June, *Chemokine receptor 5 knockout strategies*. Curr Opin HIV AIDS, 2011. 6(1): p. 74-9.
16. Duong, C. P., et al., *Cancer immunotherapy utilizing gene-modified T cells: From the bench to the clinic*. Mol Immunol, 2015.
17. Micklethwaite, K. P., et al., *Derivation of human T lymphocytes from cord blood and peripheral blood with antiviral and antileukemic specificity from a single culture as protection against infection and relapse after stem cell transplantation*. Blood, 2010. 115(13): p. 2695-703.
18. Steinman, R. M., *The dendritic cell system and its role in immunogenicity*. Annu Rev Immunol, 1991. 9: p. 271-96.
19. Ngo, M. C., et al., *Complementation of antigen presenting cells to generate T lymphocytes with broad target specificity*. J Immunother, 2014. 37(4): p. 193-203.

The invention claimed is:

1. A composition comprising HIV-antigen specific CD4$^+$ and CD8$^+$ T-cells produced by a method comprising:
   (a) separating T-cells or T-cell precursors from dendritic cells or dendritic cell precursors in a hematopoietic cell sample,
   (b) producing blasts by contacting a portion of a hematopoietic cell sample, or a portion of said separated T-cells or T-cell precursors, with PHA or another mitogen, or by CD3/CD28 stimulation, and, optionally, treating the blasts with radiation or another agent to inhibit their outgrowth;
   (c) contacting the dendritic cells or dendritic precursor cells separated in (a) with cytokine(s) or other agent(s) that generate and mature dendritic cells and with at least one HIV peptide antigen to produce HIV-antigen-presenting dendritic cells that present at least one HIV-peptide antigen, and, optionally, treating said HIV-antigen-presenting dendritic cells with radiation or another agent sufficient to inhibit their outgrowth;
   (d) contacting the T-cells or T-cell precursors from (a) with the dendritic antigen-presenting cells produced in (c) in the presence of IL-7, IL-12 and/or IL-15 to produce CD4$^+$ and CD8$^+$ HIV-antigen-specific T-cells that recognize the at least one HIV-peptide antigen;
   (e) contacting HIV-antigen-specific CD4$^+$ and CD8$^+$ T-cells produced by (d) with the blasts of (b) in the presence of the at least one HIV-peptide antigen, optionally, in the presence of K562 cells or other accessory cells in the presence of IL-2 and/or IL-15;
   (f) optionally, repeating (e) one or more times to restimulate and/or expand the HIV-antigen specific CD4$^+$ and CD8$^+$ T-cells; and
   (g) recovering HIV-antigen-specific T-cells that recognize the at least one HIV-peptide antigen;
   wherein MOGS expression has been knocked down by contacting, maintaining or culturing the T-cells, precursor T-cells or HIV-antigen specific T-cells in a medium in vitro or ex vivo containing at least one drug that inhibits or inactivates MOGS; or wherein MOGS expression has been knocked down by genetically modifying the T-cell, T-cell precursor, or HIV-antigen specific T cell to attenuate or knock out MOGS expression; or by modifying the T-cell, T-cell precursor, or HIV-antigen specific T-cell using RNAi or by expression of intrabodies to attenuate or knock out MOGS expression.

2. The composition of claim 1, wherein the hematopoietic cell sample is a cord blood sample or other sample containing naive immune cells.

3. The composition of claim 1, wherein the hematopoietic cell sample is obtained from a peripheral blood sample from a donor who is HIV-negative.

4. The composition of claim 1, wherein the hematopoietic cell sample is obtained from a peripheral blood sample from a donor who is HIV-positive.

5. The composition of claim wherein in (b) the blasts are produced using PHA, concanavalin A, pokeweed mitogen, or another mitogen.

6. The composition of claim 1, wherein in (b) the blasts are CD3/CD28 blasts produced by stimulating CD3/CD28.

7. The composition of claim 1, wherein in (b) the blasts are irradiated or chemically treated to prevent their outgrowth.

8. The composition of claim 1, wherein in (c) the separated dendritic cells or dendritic cell precursors are cultured in a dendritic cell medium containing IL-4 and GM-CSF, and then subsequently matured in a dendritic cell medium containing a mixture of IL-4, GM-CSF, IL-1B, IL-4, IL-6, PGE2, and/or TNF-α.

9. The composition of claim 1, wherein in (c) the dendritic cells are further contacted with HIV Gag, Pol, Nef and/or Env peptides or HIV Gag. Pol, Nef and/or Env peptide libraries.

10. The composition of claim 1, wherein in (c) the dendritic cells are further contacted with HIV Gag, Pol, Nef and Env peptides or HIV Gag, Pol, Nef and Env peptide libraries.

11. The composition of claim 1, wherein in (d) the T-cells or T-cell precursors from (a) are contacted with the dendritic antigen-presenting cells produced in (c) in the presence of IL-7, IL-12 and IL-15 to produce HIV-antigen-specific T-cells that recognize the at least one HIV-peptide antigen.

12. The composition of claim 1, wherein in (e) the HIV-antigen-specific CD4$^+$ and CD8$^+$ T-cells from (d) are maintained in a medium containing IL-2.

13. The composition of claim 1, wherein in (e) the HIV-antigen-specific CD4$^+$ and CD8$^+$ T-cells from (d) are maintained in a medium containing IL-15.

14. The composition of claim 1, wherein in (e) the HIV-antigen-specific CD4$^+$ and CD8$^+$ T-cells from (d) are contacted with blasts that have been pulsed with HIV Gag, Pol, Nef and/or Env peptides or HIV Gag, Pol, Nef and/or Env peptide libraries.

15. The composition of claim 1, wherein in (e) the HIV-antigen-specific CD4$^+$ and CD8$^+$ T-cells from (d) are contacted and restimulated with blasts that have been pulsed with HIV Gag, Pol, Nef and/or Env peptides or HIV Gag, Pol, Nef and/or Env peptide libraries at least three times every 5-8 days.

16. The composition of claim 1, wherein the hematopoietic cell sample has been obtained from an HIV-positive subject and steps (d) and/or (e) are performed in a medium containing amprenavir or another drug or agent that inhibits HIV replication.

17. The composition of claim 1, wherein MOGS expression has been knocked down by contacting, maintaining or culturing the T-cells, precursor T-cells or HIV-antigen specific CD4+ and CD8+ T-cells in a medium containing at least one drug that inhibits or inactivates MOGS.

18. The composition of claim 1, wherein MOGS expression has been knocked down by genetically modifying the T-cell, T-cell precursor, or HIV-antigen specific T-cell to attenuate or knock out MOGS expression; or by modifying the T-cell, T-cell precursor, or HIV-antigen specific CD4+ and CD8+ T-cell using RNAi or by expression of intrabodies to attenuate or knock out MOGS expression.

19. The composition according to claim 1, wherein said HIV-antigen specific CD4+ and CD8+ T-cells resistant to infection by human immunodeficiency virus (HIV) recognize two, three, four or more different HIV antigens.

20. A method comprising administering to a subject infected with HIV the composition according to claim 1.

21. The method of claim 20, further comprising administering to the subject a drug or agent that attenuates or knocks out MOGS expression.

22. The composition of claim 1, wherein MOGS expression has been knocked down by contacting, maintaining or culturing the T-cells, precursor T-cells or HIV-antigen specific T-cells in a medium in vitro or ex vivo containing at least one drug that inhibits or inactivates MOGS.

23. The composition of claim 1, wherein MOGS expression has been knocked down by genetically modifying the T-cell, T-cell precursor, or HIV-antigen specific T cell to attenuate or knock out MOGS expression.

24. The composition of claim 1, wherein MOGS expression has been knocked down by modifying the T-cell, T-cell precursor, or HIV-antigen specific T-cell using RNAi or by expression of intrabodies to attenuate or knock out MOGS expression.

* * * * *